(12) United States Patent
Powell et al.

(10) Patent No.: US 9,056,180 B2
(45) Date of Patent: Jun. 16, 2015

(54) TIP WITH ENCAPSULATED MARKER BAND

(75) Inventors: August L. Powell, Zimmerman, MN (US); Katherine M. Prindle, Robbinsdale, MN (US); Richard L. Goodin, Blaine, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2244 days.

(21) Appl. No.: 11/127,525

(22) Filed: May 12, 2005

(65) Prior Publication Data

US 2006/0258982 A1    Nov. 16, 2006

(51) Int. Cl.
*A61M 31/00* (2006.01)
*A61M 25/00* (2006.01)
*A61M 25/01* (2006.01)

(52) U.S. Cl.
CPC .......... *A61M 25/001* (2013.01); *A61M 25/0068* (2013.01); *A61M 25/0108* (2013.01); *A61M 2025/0081* (2013.01)

(58) Field of Classification Search
CPC ............... A61M 2025/0081; A61M 25/001; A61M 25/0068; A61M 25/0108
USPC ............... 604/96.01, 164.01, 523–532, 103.1
See application file for complete search history.

(56) References Cited

U.S. PATENT DOCUMENTS

| | | | |
|---|---|---|---|
| 4,571,240 A | 2/1986 | Samson et al. | 604/96 |
| 4,938,220 A | 7/1990 | Mueller, Jr. | 128/658 |
| 5,045,071 A | 9/1991 | McCormick et al. | 604/280 |
| 5,429,617 A * | 7/1995 | Hammersmark et al. | 604/264 |
| 5,458,615 A * | 10/1995 | Klemm et al. | 606/198 |
| 5,762,637 A * | 6/1998 | Berg et al. | 604/264 |
| 6,652,507 B2 * | 11/2003 | Pepin | 604/523 |
| 6,970,734 B2 * | 11/2005 | Eidenschink et al. | 600/424 |
| 7,322,988 B2 * | 1/2008 | Sterud et al. | 606/108 |
| 7,641,647 B2 * | 1/2010 | Gunderson | 604/529 |
| 2001/0003297 A1 * | 6/2001 | Pedersen et al. | 156/296 |
| 2004/2672063 | 12/2004 | Potter et al. | 604/164.05 |

FOREIGN PATENT DOCUMENTS

| | | |
|---|---|---|
| EP | 0303487 | 2/1989 |
| EP | 0513836 | 11/1992 |
| JP | 64-068276 | 3/1989 |
| JP | 6339530 | 12/1994 |
| WO | 03/020353 | 3/2003 |

OTHER PUBLICATIONS

U.S. Appl. No. 11/224,416, filed Sep. 12, 2005, Moberg et al.

* cited by examiner

*Primary Examiner* — Kami A Bosworth
*Assistant Examiner* — Imani Hayman
(74) *Attorney, Agent, or Firm* — Vidas, Arrett & Steinkraus

(57) ABSTRACT

A catheter tip assembly comprises a marker band and a catheter tip. The catheter tip has an inner lumen therethrough and an outer portion and an inner portion with the marker band disposed therebetween.

10 Claims, 4 Drawing Sheets

TIP WITH ENCAPSULATED MARKER BAND

CROSS-REFERENCE TO RELATED APPLICATIONS

Not Applicable

STATEMENT REGARDING FEDERALLY SPONSORED RESEARCH

Not Applicable

BACKGROUND OF THE INVENTION

This invention relates generally to catheters, and more specifically to an assembly and method that may be used for delivering and deploying one or more implantable medical devices, including without limitation, stents, grafts, stent-grafts, vena cava filters, or other implantable medical devices within a body lumen.

When advancing a catheter through a body lumen radiopaque marker bands are sometimes contained within the tips in order to better locate the position of the catheter during a medical procedure.

Delivery catheters, such as disclosed in U.S. Pat. No. 6,007,543 and incorporated herein by reference, are known in the art. Such catheters may include radiopaque marker bands and stent securement rings as disclosed in U.S. Pat. No. 6,530,947, U.S. Pat. No. 6,315,790 and U.S. Pat. No. 6,395,008, also incorporated by reference.

Some known catheter tips that are equipped with marker bands are injection molded such that the outside diameter of the marker band is molded into the tip while the interior diameter of the marker band is exposed to an inner or guidewire lumen. This exposure makes the marker band vulnerable to being dislodged or damaged while being inserted over a guidewire or when retracting the guidewire, thereby posing a safety hazard.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a catheter tip assembly may comprise a marker band and a catheter tip having an inner lumen therethrough. The catheter tip may have an outer portion and an inner portion with the marker band disposed therebetween. In at least one embodiment, the inner portion may be constructed of a different material than the outer portion.

In at least one embodiment, the inner portion fully separates the marker band from the lumen. In at least one embodiment the marker band may be characterized as being encapsulated between the inner portion and the outer portion of the catheter tip.

In at least one embodiment, the outer portion may be constructed of material selected from the group consisting of thermoplastic polyurethane (e.g. PELLETHANE® from Dow), polyolefin, silicone, etc.

In at least one embodiment, the inner portion may be constructed of material selected from the group consisting of thermoplastic polyurethane (e.g. PELLETHANE® from Dow), polyolefin, silicone, etc.

In at least one embodiment, the outer portion may be fused to the inner portion.

In at least one embodiment, the catheter tip assembly may be affixed to a catheter.

In at least one embodiment, the entire outer portion and/or the inner portion may extend longitudinally for the length of the marker band. In at least one embodiment, the inner portion may be comprised of strips.

In at least one embodiment, the inner portion does not fully separate the marker band from the inner lumen.

In at least one embodiment, the invention is directed to one or more methods of manufacturing a catheter tip assembly.

These and other embodiments of the invention are pointed out with particularity in the claims annexed hereto and forming a part hereof. However, for additional understanding of the invention, its advantages and objectives obtained by its use, reference should be made to the drawings which form a further part hereof and the accompanying descriptive matter, in which there is illustrated and described various embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
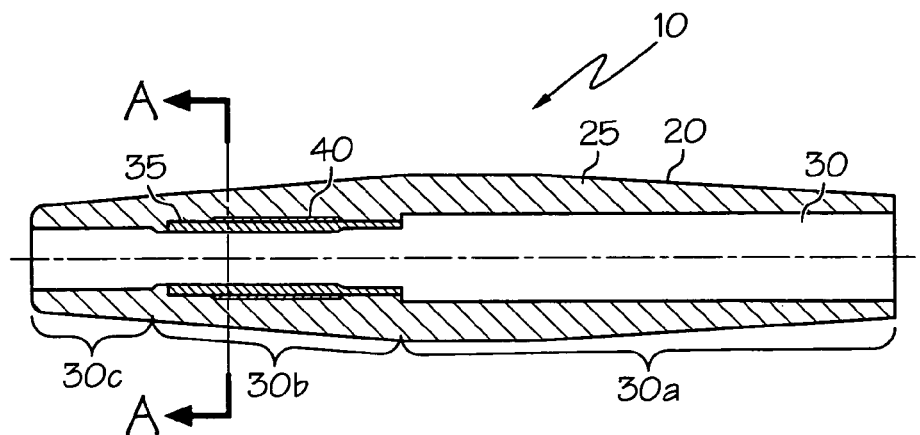
FIG. 1 illustrates a cross-sectional side view of an embodiment of a catheter tip assembly in accordance with the present invention.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring generally to FIG. 1, a cross-sectional side view of a catheter tip assembly 10 is shown. The catheter tip assembly 10 includes a catheter tip 20 having an inner lumen 30 such as for passage of a guidewire (not shown) therethrough. The inner lumen 30 shown here comprises a proximal region 30a, an intermediate region 30b, and a distal region 30c. The lumen regions 30a, 30b, and 30c can have the same or different diameters. A marker band 40 can be disposed about any portion of the lumen 30. In the embodiment shown, the marker band is disposed about the intermediate region 30b of the lumen 30. In at least one embodiment the proximal region 30a is sized to fit over the inner shaft of a catheter, such as catheter 5 shown in FIG. 9. When the tip 20 is positioned over the catheter shaft 15 in the manner shown in FIG. 9, the intermediate region 30b can be immediately adjacent to the distal end 6 of the catheter shaft 15. It should be noted that the marker band 40 can also be disposed in the distal region 30c and/or the proximal region 30a. It should further be noted that one or more marker bands 40 can be positioned in the catheter tip 10 about any or all regions 30a, 30b, and 30c, or portions thereof. Additionally, the marker band 40 can also have a flared portion 42 as shown in FIGS. 3a and 3c.

Figure 2:
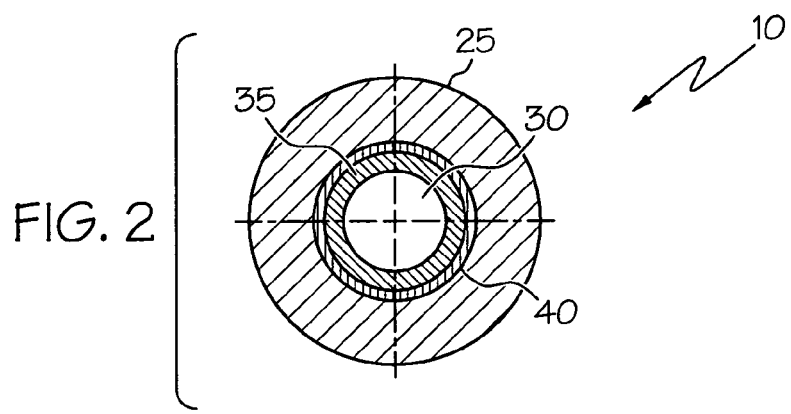
FIG. 2 illustrates a cross-sectional view of an embodiment of an inventive catheter tip at section A-A.

The catheter tip 20, as shown in FIG. 1, comprises an outer tip portion 25 and an inner tip portion 35. In this embodiment, the outer tip portion 25 comprises the majority of the catheter tip 20. In some embodiments, the inner tip portion 35 comprises the majority of the catheter tip 20. In some embodiments the outer tip portion 25 comprises all of the catheter tip assembly 10 except the marker bands 40 and the inner tip portion 35. In some embodiments, the inner tip portion is a tube, and in some embodiments more specifically a polymer tube. In some embodiments the outer tip portion 25 is disposed about a marker band 40. In some embodiments, the marker band 40 is disposed about inner tip portion 35. FIG. 2 is a cross sectional view of catheter tip assembly 10 along line A-A and further illustrates the outer tip portion being disposed about marker band 40 and the markers 40 being disposed about inner tip portion 35. In some embodiments, the longitudinal lengths of the outer portion, inner portion, and the marker band are different; the marker band need not extend over the entire length of the interface between the inner portion and the outer portion.

In at least one embodiment, the outer tip portion 25 and the inner tip portion 35 are comprised of different materials. In at least one embodiment, the outer tip portion 25 is constructed of soft, resilient polymers such as thermoplastic polyurethane (e.g. PELLETHANE® from Dow), polyolefin, silicone, DYNAFLEX® thermoplastic elastomers, KRATON® thermoplastic elastomers, etc.

In at least one embodiment, the outer tip portion 25 and/or the inner tip portion 35 can be constructed of any suitable material, such as polyesters and copolymers thereof such as those sold including polyalkylene terephthalates such as polyethylene terephthalate (PET) and polybutylene terephthalate (PBT) available under the tradename of EKTAR® available from Eastman Chemical Co. in Kingsport, Tenn., polycyclohexylene terephthalate (PCT); poly(trimethylene terephthalate) (PTT), PCTG and poly(cyclohexanedimethanol-co-ethylene terephthalate) (PETG) copolyesters available under the tradename of EASTAR® available from Eastman Chemical Co., PCTA available under the tradename of DURASTAR® available from Eastman Chemical Co., poly (ethylene naphthalate) (PEN) polyester available from DuPont in Wilmington, Del. under the tradename of TEONEX®; and so forth; polyester elastomers (PEELs); polyamides such as amorphous nylon and nylon 12 such as those available from Elf Atochem under the tradename of CRISTAMID® and copolymers thereof such as GRILAMID® TR-55-LX nylon 12 polyether-block-amide available from EMS-American Grilon in Sumter, S.C.; polyetherimides available from GE Plastics under the tradename of ULTEM®; polystyrene and expandable polystyrene (EPS); acrylonitrile-butadiene-styrene (ABS); styrene-acrylonitrile (SANs); polyphenylene sulfide (PPS); polyphenylene oxides (PPO); interpolymers of PPO and EPS; polyetherketones (PEEK); polyolefins such as polyethylenes and polypropylenes including low, medium and high densities such as HDPE available under the tradename of ALATHON® from Equistar Chemicals; amorphous polyolefins; polyether-block-amides such as those sold under the tradename of PEBAX® available from Elf Atochem; polyimides; polyurethanes; polycarbonates; polyethers; silicones; as well as any copolymers thereof. The above list is intended for illustrative purposes only, and is not intended to limit the scope of the present invention. One of ordinary skill in the art has knowledge of such polymeric materials.

In at least one embodiment the marker band 40 comprises radiopaque marker bands, MRI suitable marker bands, and the like. Marker band 40 can be of any suitable shape and desirably comprises one or more circumferential bands. In at least one embodiment, the marker band 40 is comprised of a metal. In at least one embodiment, the metal of the marker band 40 is gold, platinum, platinum iridium, or any combination thereof.

In at least one embodiment, the marker band 40 is not in communication with the inner lumen 30. In some embodiments such as are shown in FIGS. 1 and 2 the inner tip portion 35 can be a constructed of a single sheet of material such that the marker band 40 is encapsulated between the inner tip portion 35 and the outer tip portion 25. In such an embodiment, the inner lumen 30 can be separated from the marker band 40 such that the marker band does not come into contact with the inner lumen during delivery.

Figure 3:
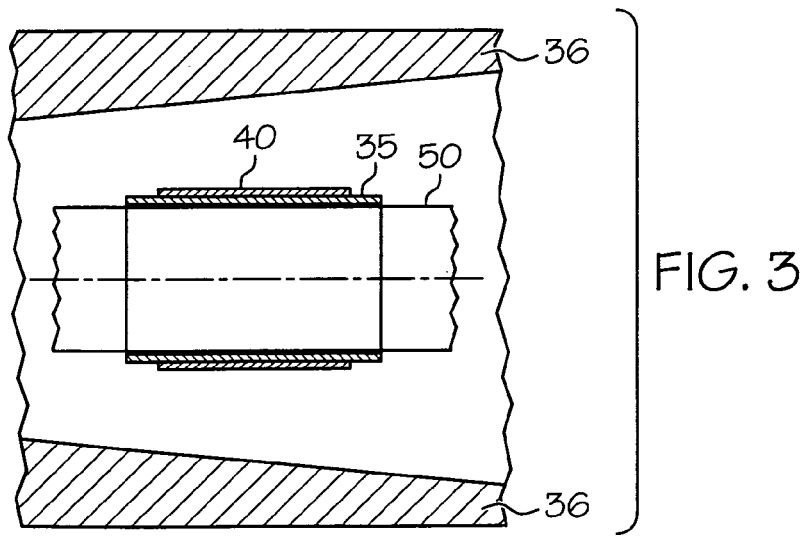
FIG. 3 illustrates a cross-sectional side view of a tube and marker band used in a catheter tip assembly disposed about a core pin or mandrel.
Figure 3A:
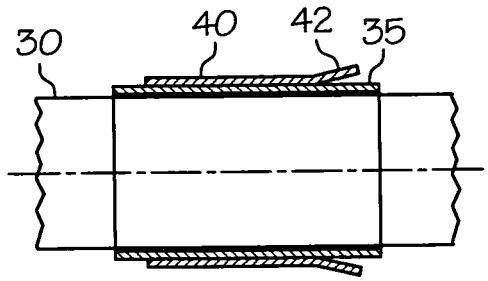
FIG. 3a illustrates a cross-sectional side view of a tube and flared marker band used in a catheter tip assembly disposed about a core pin or mandrel.

In at least one embodiment, manufacturing the catheter tip assembly 10 can include disposing the inner portion 35 on a core pin or mandrel 50 as shown in FIG. 3. The inner portion 35 preferably extends beyond the edges of the marker band 40 such that the ends of the inner portion 35 can fuse with the outer portion 25 when molding the catheter tip 20. In at least one embodiment the mandrel or core pin 50 and the inner portion 35 and marker band 40 as arranged in FIG. 3 are placed within an injection mold 36 where the inner portion 35 then fuses with the molten outer portion 25 as the catheter tip 20 is formed.

In at least one embodiment the marker band(s) 40 can be flared as shown in FIG. 3a. The flared portion 42 of the marker band 40 can aid in embedding the marker band into the tip material of a catheter tip 20 (the tip 20 shown in FIG. 1). The flared portion 42 can make the marker band more resistant to dislodging as the tip is pushed against an object.

Figure 3B:
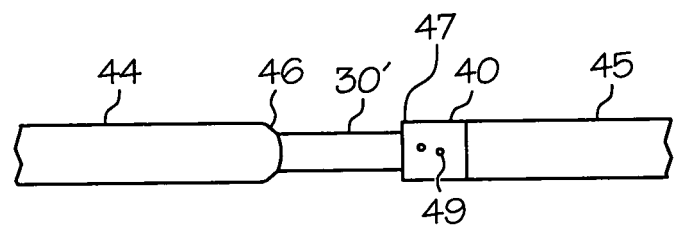
FIG. 3b illustrates a side view of a device for flaring out a portion of the marker band and the marker band disposed thereon.
Figure 3C:
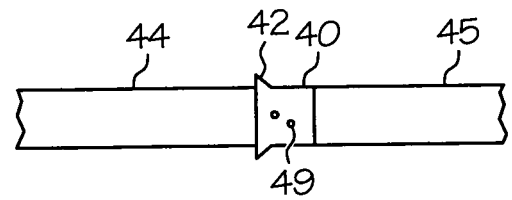
FIG. 3c illustrates a side view of a device for flaring out a portion of the marker band and the marker band disposed thereon and having a portion flared out.

In at least one embodiment the flared portion 42 of the marker band 40 may be formed by using a hypotube 44 having a rounded end 46 and a hypotube 45 having a straight end 47 as shown in FIGS. 3*b* and 3*c*. It should be noted that any tube or cylindrical device may be used in place of the hypotubes and that the rounded end may alternatively be conical or frustoconical. In some instances only one tube 44 or 45 is used.

In FIG. 3*b* a non-flared marker band 40 and hypotubes 44 and 45 are disposed about a mandrel 30'. In FIG. 3*c* hypotube 44 having a rounded end 46 is rotated and moved longitudinally along the mandrel 30'. The rounded end 46 can be forced partially within the lumen of the marker band 40 and thereby flare out an edge of the marker band 40. The marker band 40 can then be removed from the mandrel 30' and disposed about the mandrel/pin 30 as shown in FIG. 3*a*.

Though not necessary, the marker band 40 can have small holes 49 as shown in FIGS. 3*b* and 3*c*. The holes can improve adherence of the band 40 to a catheter tip.

Figure 4:
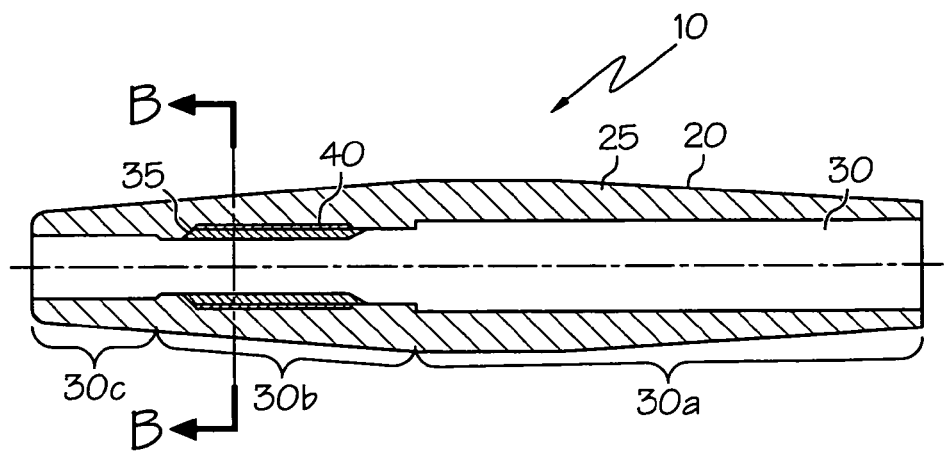
FIG. 4 illustrates a cross-sectional side view of an embodiment of a catheter tip assembly in accordance with the present invention.

In some embodiments, the inner portion 35 can be formed at the same (or different) time as the outer portion 25. In some embodiments, the inner portion 35 and outer portion 25 are constructed of the same material as shown in FIG. 4. Some of the acceptable materials are listed above beginning on line 9 of page 5.

Figure 5:
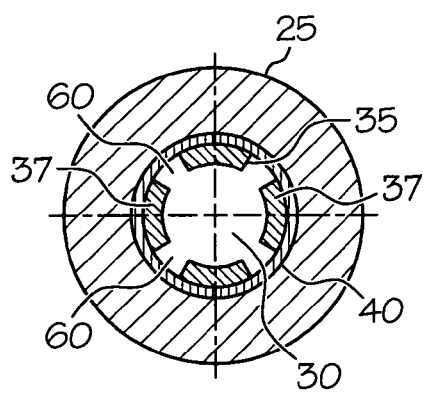
FIG. 5 illustrates a cross-sectional view of an embodiment of an inventive catheter tip at section B-B.

In at least one embodiment, an example of which is shown in FIG. 5, the inner portion 35 is comprised of strips 37 of material extending in a longitudinal direction separated by gaps 60. In some embodiments, the strips protect the marker band 40 from contact with a guidewire disposed within the lumen 30. In some embodiments, there is only one strip 37; in other embodiments there can be a plurality of strips 37. A single strip can be designed such that it almost completely covers the entire marker band 40 leaving only a small gap 60.

Figure 6:
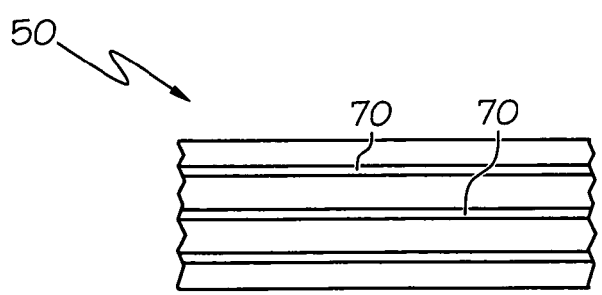
FIG. 6 illustrates a side view of a core pin or mandrel having longitudinal grooves.
Figure 7:
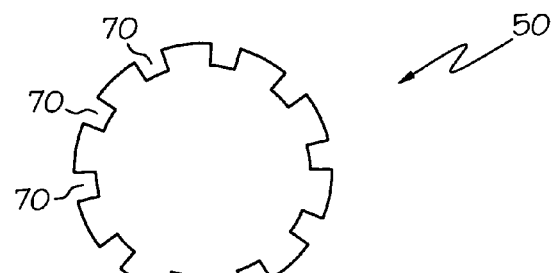
FIG. 7 illustrates a cross-sectional view of the core pin or mandrel having longitudinal grooves.

In at least one embodiment, the strips 37 are formed when a core pin or mandrel 50 having grooves 70, as shown in FIGS. 6 and 7, is used during the molding of the catheter tip assembly 10. The grooves 70 can extend the length of the mandrel 50. In some embodiments, the grooves extend parallel to the longitudinal axis of the mandrel 50. In some embodiments, the grooves swirl or spiral around the mandrel 50 or extend in some other pattern or arrangement. In some embodiments, the grooves are intermittent and/or do not extend for the full length of the mandrel 50 and/or the full length of the marker band 40.

Figure 8:
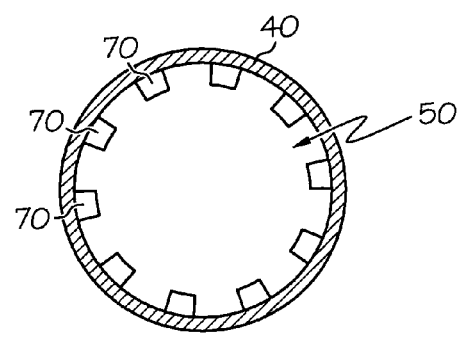
FIG. 8 illustrates a cross-sectional view of the core pin or mandrel having longitudinal grooves and a marker band disposed about the mandrel.

In some embodiments, the catheter tip assembly is manufactured by molding and including the step of disposing a marker band 40 about the mandrel 50 having grooves 70 as shown in FIG. 8. In at least one embodiment the mandrel 50 and the marker band 40 as arranged in FIG. 8 can be placed within an injection mold where the molten catheter tip material flows over the marker band 40 and within the grooves 70 of the mandrel under the marker band 40 to form both an outer and inner portion of the catheter tip.

Figure 9:
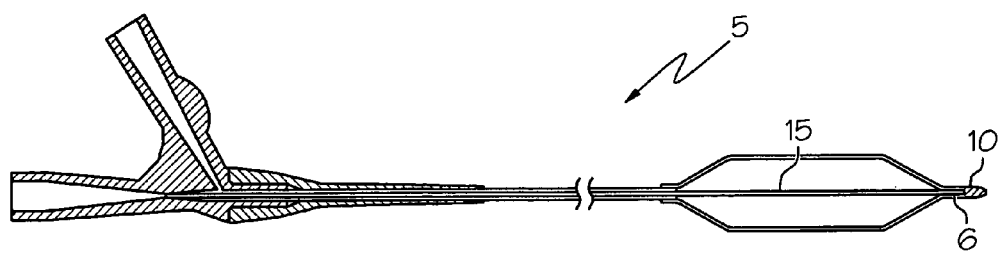
FIG. 9 illustrates a cross-sectional view of a catheter tip assembly affixed to a catheter.

FIG. 9 illustrates a catheter tip assembly 10 affixed to the inner shaft 15 of a catheter 5. In at least one embodiment the catheter tip assembly 10 can be molded over a catheter inner shaft 15 such that the catheter tip assembly bonds to the catheter shaft. In at least one embodiment the catheter tip assembly 10 is injection molded and then adhesively bonded and/or thermally bonded to the catheter shaft 15. In at least one embodiment the assembly 10 can be mechanically engaged to the catheter 5. In at least one embodiment the assembly 10 can be threadedly engaged.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of various embodiments of the invention. Those skilled in the art may recognize other equivalents to the specific embodiment described herein which equivalents are intended to be encompassed by the claims attached hereto.

The invention claimed is:

1. A catheter tip assembly comprising:
a catheter tip having a lumen therethrough, the catheter tip having an outer portion disposed about a marker band and an inner portion about which the marker band is disposed, the inner portion comprising strips that extend longitudinally along the length of the marker band, the strips are separated by gaps.

2. The catheter tip assembly of claim 1 wherein the inner portion is constructed of a material different than the material of the outer portion.

3. The catheter tip assembly of claim 1 wherein both the outer portion and the inner portion are constructed of a polymeric material.

4. The catheter tip assembly of claim 1 wherein both the outer portion and the inner portion are constructed of material selected from the group consisting of polyurethane, polyolefin, silicone, or any combination thereof.

5. The catheter tip assembly of claim 1 wherein the outer portion is fused to the inner portion.

6. The catheter tip assembly of claim 1 wherein the inner portion does not fully separate the marker band from the inner lumen.

7. The catheter tip assembly of claim 1 wherein the marker band has a flared portion.

8. The catheter tip assembly of claim 1 wherein the marker band is a tube having a lumen, the tube having at least one hole in communication with the lumen.

9. A catheter assembly comprising:
a catheter, the catheter comprising an inner catheter shaft, a marker band and a catheter tip, the catheter tip having an inner lumen therethrough and an outer portion and an inner portion with the marker band disposed therebetween, the inner portion constructed of a different material than the outer portion, the outer portion fused to the inner portion so as to encapsulate the marker band, and the catheter tip affixed to the catheter, the catheter tip comprising a proximal region configured and sized to fit over the inner catheter shaft.

10. A catheter assembly comprising:

a catheter, a marker band and a catheter tip, the catheter tip having an inner lumen therethrough and an outer portion and an inner portion with the marker band disposed therebetween, the inner portion constructed of a different material than the outer portion, the outer portion fused to the inner portion so as to encapsulate the marker band, and the catheter tip affixed to the catheter, the outer portion, inner portion and the marker band are defined by different longitudinal lengths, the outer portion and inner portion having an interface therebetween, the marker band having a longitudinal length that does not extend over the entire interface between the inner portion and the outer portion, the inner portion is fused to the outer portion encapsulating the longitudinal length of the marker band.

* * * * *